(12) United States Patent
Sikora et al.

(10) Patent No.: US 10,709,562 B2
(45) Date of Patent: Jul. 14, 2020

(54) DEVICES, APPARATUSES, KITS, AND METHODS FOR ANCHORING A SUTURE TO A BONE

(71) Applicant: Arthrosurface, Inc., Franklin, MA (US)

(72) Inventors: George Sikora, Bridgewater, MA (US); Steven Ek, Bolton, MA (US)

(73) Assignee: ARTHROSURFACE, INC., Franklin, MA (US)

(*) Notice: Subject to any disclaimer, the term of this patent is extended or adjusted under 35 U.S.C. 154(b) by 240 days.

(21) Appl. No.: 15/445,075

(22) Filed: Feb. 28, 2017

(65) Prior Publication Data

US 2017/0360566 A1 Dec. 21, 2017

Related U.S. Application Data

(60) Provisional application No. 62/300,903, filed on Feb. 28, 2016, provisional application No. 62/300,905, filed on Feb. 28, 2016.

(51) Int. Cl.
*A61F 2/30* (2006.01)
*A61B 17/04* (2006.01)
(Continued)

(52) U.S. Cl.
CPC ...... *A61F 2/30734* (2013.01); *A61B 17/0401* (2013.01); *A61B 17/1617* (2013.01);
(Continued)

(58) Field of Classification Search
CPC .......... A61F 2310/00359; A61F 2/0059; A61F 2/28; A61F 2/30; A61F 2/30734; A61F 2/30771; A61F 2/4014; A61F 2/46; A61F 2/4601; A61F 2/4612; A61F 2/4644; A61F 2/4657; A61F 2002/2835; A61F 2002/2839; A61F 2002/30001; A61F 2002/30108; A61F 2002/3011; A61F 2002/30113; A61F 2002/30115; A61F 2002/300224; A61F 2002/30827; A61F 2002/30649; A61F 2002/30822; A61F 2002/3082; A61F 2002/30789; A61F 2002/30785; A61F 2002/30784; A61F 2002/30772; A61F 2002/30736; A61F 2002/4623; A61F 2002/4624; A61F 2002/4627; A61F 2002/4628; A61F 2002/4638; A61F 2002/464; A61F 2002/4662;
(Continued)

(56) References Cited

U.S. PATENT DOCUMENTS

| 6,368,322 B1* | 4/2002 | Luks | A61B 17/861 |
| | | | 606/308 |
| 2002/0004660 A1* | 1/2002 | Henniges | A61B 17/1655 |
| | | | 606/86 B |

(Continued)

*Primary Examiner* — Robert A Lynch
(74) *Attorney, Agent, or Firm* — Norton Rose Fulbright US LLP (57) ABSTRACT

Embodiments of devices, apparatuses, kits, and methods for repairing a human joint by suturing biological tissue to the articular surface of a bone at the joint (e.g., repairing defects in the humerus at the glenoid joint after an anterior shoulder dislocation) are described herein. Biological tissue may include hard tissue such as bone or a joint socket or soft tissue such as cartilage, ligaments, tendons, or muscle tissue.

19 Claims, 11 Drawing Sheets

(51) Int. Cl.
 A61B 17/17 (2006.01)
 A61B 17/16 (2006.01)
 A61F 2/46 (2006.01)
 A61B 17/56 (2006.01)
 A61B 90/00 (2016.01)
 A61F 2/40 (2006.01)
 A61B 17/00 (2006.01)

(52) U.S. Cl.
 CPC ...... *A61B 17/1796* (2013.01); *A61F 2/30771* (2013.01); *A61F 2/4612* (2013.01); *A61F 2/4657* (2013.01); *A61B 17/1615* (2013.01); *A61B 2017/00933* (2013.01); *A61B 2017/0403* (2013.01); *A61B 2017/0404* (2013.01); *A61B 2017/0409* (2013.01); *A61B 2017/0414* (2013.01); *A61B 2017/0438* (2013.01); *A61B 2017/0445* (2013.01); *A61B 2017/0464* (2013.01); *A61B 2017/564* (2013.01); *A61B 2090/034* (2016.02); *A61B 2090/062* (2016.02); *A61F 2/4014* (2013.01); *A61F 2/4603* (2013.01); *A61F 2002/30649* (2013.01); *A61F 2002/30736* (2013.01); *A61F 2002/30785* (2013.01); *A61F 2002/30828* (2013.01); *A61F 2002/30935* (2013.01); *A61F 2002/4022* (2013.01); *A61F 2002/4662* (2013.01); *A61F 2310/00011* (2013.01); *A61F 2310/00359* (2013.01)

(58) Field of Classification Search
 CPC .... A61B 2017/0409; A61B 2017/0414; A61B 2017/0438; A61B 2017/0456; A61B 2017/0458; A61B 2017/0459; A61B 2017/564
 See application file for complete search history.

(56) References Cited

U.S. PATENT DOCUMENTS

| | | | | |
|---|---|---|---|---|
| 2008/0262616 | A1* | 10/2008 | McKay | A61B 17/1635 623/14.12 |
| 2009/0306711 | A1* | 12/2009 | Stone | A61B 17/0401 606/232 |
| 2010/0063542 | A1* | 3/2010 | van der Burg | A61B 17/0401 606/232 |
| 2010/0191245 | A1* | 7/2010 | Ek | A61B 17/1675 606/88 |
| 2012/0204521 | A1* | 8/2012 | Webb | B65B 31/06 53/507 |
| 2013/0110163 | A1* | 5/2013 | Ballard | A61B 17/0401 606/232 |

\* cited by examiner

DEVICES, APPARATUSES, KITS, AND METHODS FOR ANCHORING A SUTURE TO A BONE

CROSS-REFERENCE TO RELATED APPLICATIONS

This application claims the benefit of U.S. Provisional Application No. 62/300,903, filed Feb. 28, 2016, and U.S. Provisional Application No. 62/300,905, filed Feb. 28, 2016, the contents of each of which applications are incorporated herein by reference in their respective entireties.

FIELD OF INVENTION

The present invention relates generally to orthopedic treatments, and more particularly, but not by way of limitation, to devices, apparatuses, kits, and methods for repairing a joint by suturing biological matter to an articular surface of a bone.

DESCRIPTION OF RELATED ART

Articular surfaces of bones may sometimes be damaged. For example, after an anterior shoulder dislocation, a patient's shoulder may suffer various forms of structural damage. Examples may include Bankart tears to shoulder ligaments, tears to rotator cuff ligaments, damage to the rim of the glenoid, and damage to the articular head of the humerus such as a Hill-Sachs lesion. In some instances, damage to the humerus may require surgical repair such as capsular shifting or bone and/or tissue grafting. In order to successfully repair the joint, the surgeon must be able to affix or suture bone or soft tissue into or over the defect in the articular surface of the bone.

In some instances, it is desirable to anchor tissue (e.g., soft tissue) to a bone. Examples include repairing torn ligaments and/or re-attaching soft tissue after a joint replacement.

SUMMARY

This disclosure includes embodiments of devices, apparatuses, kits, and methods for repairing a joint by suturing biological matter to an articular surface of a bone. Some such embodiments of the devices, apparatuses, kits, and methods are for affixing biological matter to a bone to repair a defect in an articular surface of the bone.

Some embodiments of the present devices comprise: a cylindrical body comprising a coupling end, a surface end, a peripheral surface extending at least partially between the coupling end and the surface end, the body defining one or more suture holes extending inward from the peripheral surface, the body configured to be coupled into a mating cavity of a bone adjacent to a selected type of human joint socket such that: (i) the coupling end faces a bottom surface defining the mating cavity, (ii) the surface end augments an articular surface of the bone, and (iii) the peripheral surface faces a sidewall defining the mating cavity.

Some embodiments of the present devices further comprise: a coupling surface extending between the peripheral surface and the surface end.

Some embodiments of the present devices further comprise: one or more sutures configured to attach to the body via the one or more suture holes.

In some embodiments of the present devices, the body further configured to rotate within the mating cavity.

In some embodiments of the present devices, the body defines one or more grooves disposed on the peripheral surface, the one or more grooves configured to receive the one or more sutures between the peripheral surface and the mating cavity as the body rotates within the mating cavity. In some embodiments, the one or more grooves comprise a single groove disposed around the entire perimeter of the peripheral surface. In some embodiments, the one or more grooves comprise two grooves each disposed around half of the perimeter of the peripheral surface. In some embodiments, the one or more grooves comprise a plurality of grooves each disposed around a portion of the perimeter of the peripheral surface, the plurality of grooves being offset from each other along the longitudinal axis of the peripheral surface. In some embodiments, the one or more grooves comprise a plurality of grooves each disposed in an angled helical configuration on the peripheral surface.

In some embodiments of the present devices, the body defines one or more suture holes extending inward from the peripheral surface, each of the one or more suture holes configured to receive a suture. In some embodiments, the one or more suture holes are aligned with the one or more grooves. In some embodiments, the one or more suture holes comprise a single hole passing entirely through the body. In some embodiments, the one or more suture holes comprise a single hole passing partially through the body. In some embodiments, the one or more suture holes comprise two holes passing partially through the body. In some embodiments, the one or more suture holes comprise a plurality of holes passing through the body, the plurality of holes being offset from each other along the longitudinal axis of the peripheral surface. In some embodiments, the one or more suture holes each has a longitudinal axis that is perpendicular to a central longitudinal axis of the body.

In some embodiments of the present devices, the body is configured to be removably coupled to a driver such that the body can be rotated via rotation of the driver. In some embodiments, the body defines a plurality of axial holes extending through the surface end toward the coupling end, the plurality of holes configured to receive a plurality of prongs of the driver such that the body can be rotated via rotation of the driver. In some embodiments, the body defines a plurality of axial holes extending through the surface end toward the coupling end, the plurality of holes configured to receive a plurality of prongs of the driver such that the body can be rotated via rotation of the driver. In some embodiments, the plurality of axial holes passes entirely through the body. In some embodiments, each of the plurality of axial holes passes partially through the body. In some embodiments, the one or more axial holes each has a central longitudinal axis that is substantially parallel to a longitudinal axis of the body.

In some embodiments of the present devices, the body comprises a plurality of axial grooves disposed into the coupling surface, the plurality of grooves configured to receive a plurality of prongs of a removable driver such that the body can be rotated via rotation of the driver. In some embodiments, each of the plurality of axial grooves extends entirely between the surface end and the peripheral surface. In some embodiments, each of the plurality of axial grooves extends partially between the surface end and the peripheral surface. In some embodiments, each of the one or more axial grooves are substantially parallel to a longitudinal axis of the body.

In some embodiments of the present devices, the body comprises a biological material. In some embodiments, the biological material comprises bone. In some embodiments, the body comprises a metallic material. In some embodiments, the body comprises a polymer material.

Some embodiments of the present apparatuses comprise: a driver having a shaft, a handle (e.g., attached to the distal end of the shaft), and a plurality of prongs (e.g., attached to the proximal end of the shaft) configured to be inserted at a surface side of a body. Some embodiments further comprise: a pin having a first end, a second end, and a depth indicator, the pin configured to have the first end inserted into an articular surface of a bone to a depth indicated by the depth indicator such that the second end of the pin extends a predetermined distance out of the bone. Some embodiments further comprise: a reamer configured to be disposed over the second end of the pin when the first end of the pin is disposed in the bone, and rotated to remove a portion of the bone to form a mating cavity in the articular surface of the bone. In some embodiments, the reamer comprises a cutting end, a distal end, and an elongated passage extending from the cutting end toward the distal end, the passage configured to receive at least a portion of the pin. In some embodiments, the reamer comprises a shoulder in the passage, the shoulder configured to contact the second end of the pin to provide a cutting depth limit, the cutting depth limit corresponding to a depth less than or equal to the length of the body. In some embodiments, the reamer is configured to remove a portion of the bone to form one or more notches along a perimeter of the mating cavity, the one or more notches configured to enable an alignment of the body with the mating cavity.

Some embodiments of the present kits comprise: an embodiment of the present devices; and an embodiment of the present apparatuses; where the device and apparatus are disposed in one or more sealed packages.

Some embodiments of the present methods (e.g., of anchoring a suture to bone, of repairing a human joint) comprise: inserting a cylindrical body of a device into a mating cavity formed in a bone, where the body comprises a coupling end, a surface end, a peripheral surface extending between the coupling end and the surface end, the body defining one or more suture holes extending inward from the peripheral surface, the device having one or more sutures extending out of the one or more suture holes; where the body is inserted into the mating cavity such that: (i) the coupling end faces a bottom surface defining the mating cavity, (ii) the surface end augments an articular surface of the bone, (iii) the peripheral surface faces a sidewall defining the mating cavity; and (iv) the one or more sutures are at least partially disposed between the body and the sidewall to resist removal of the body from the mating cavity. In some embodiments, the mating cavity is formed in a bone and disposed adjacent to a human joint socket.

Some embodiments of the present methods further comprise: rotating the body after the body is inserted into the mating cavity.

In some embodiments of the present methods, the suture is coupled to soft tissue. Some embodiments of the present methods further comprise: coupling the suture to soft tissue before the body is inserted into the mating cavity, or before the body is rotated in the mating cavity.

In some embodiments of the present methods, the body further comprises a coupling surface extending between the peripheral surface and the surface end.

Some embodiments of the present methods further comprise: shaping, prior to coupling the body to the bone, the mating cavity in the bone to correspond to the shape of the coupling end and peripheral surface of the body. In some embodiments, shaping comprises: inserting a pin having a first end, a second end, and a depth indicator into an articular surface of the bone to a depth indicated by the depth indicator; disposing a reamer comprising a cutting end, a distal end, and an elongated passage extending from the cutting end toward the distal end over the second end of the pin and rotating the reamer to shape the mating cavity and provide an optional notch; and removing the reamer and the pin.

Some embodiments of the present methods further comprise: inserting one or more sutures through the one or more suture holes before inserting the body into the mating cavity.

Some embodiments of the present methods further comprise: inserting a plurality of prongs of a removable driver into one or more holes disposed through or on the body, the one or more holes each configured to receive a prong; and removing the prongs from the holes after the body is inserted into the bone. In some embodiments, the one or more holes comprise one or more grooves disposed on the coupling surface, the one or more grooves each configured to receive one of the plurality of prongs.

Some embodiments of the present methods further comprise: tensioning the one or more sutures along a longitudinal axis of the body.

In some embodiments of the present methods, the one or more sutures are configured to attach to soft tissue and couple the soft tissue to the bone.

In some embodiments of the present methods, inserting the body into the mating cavity comprises rotating the removable driver until the body is secured within the mating cavity.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees, and substantially parallel includes parallel), as understood by a person of ordinary skill in the art. In any embodiment of the present devices, apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device, or structure that is configured in a certain way is configured in at least that way, but it can also be configured in other ways than those specifically described.

Any embodiment of any of the present devices, apparatuses, kits, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiments depicted in the figures.

DESCRIPTION OF ILLUSTRATIVE EMBODIMENTS

Figure 1A:
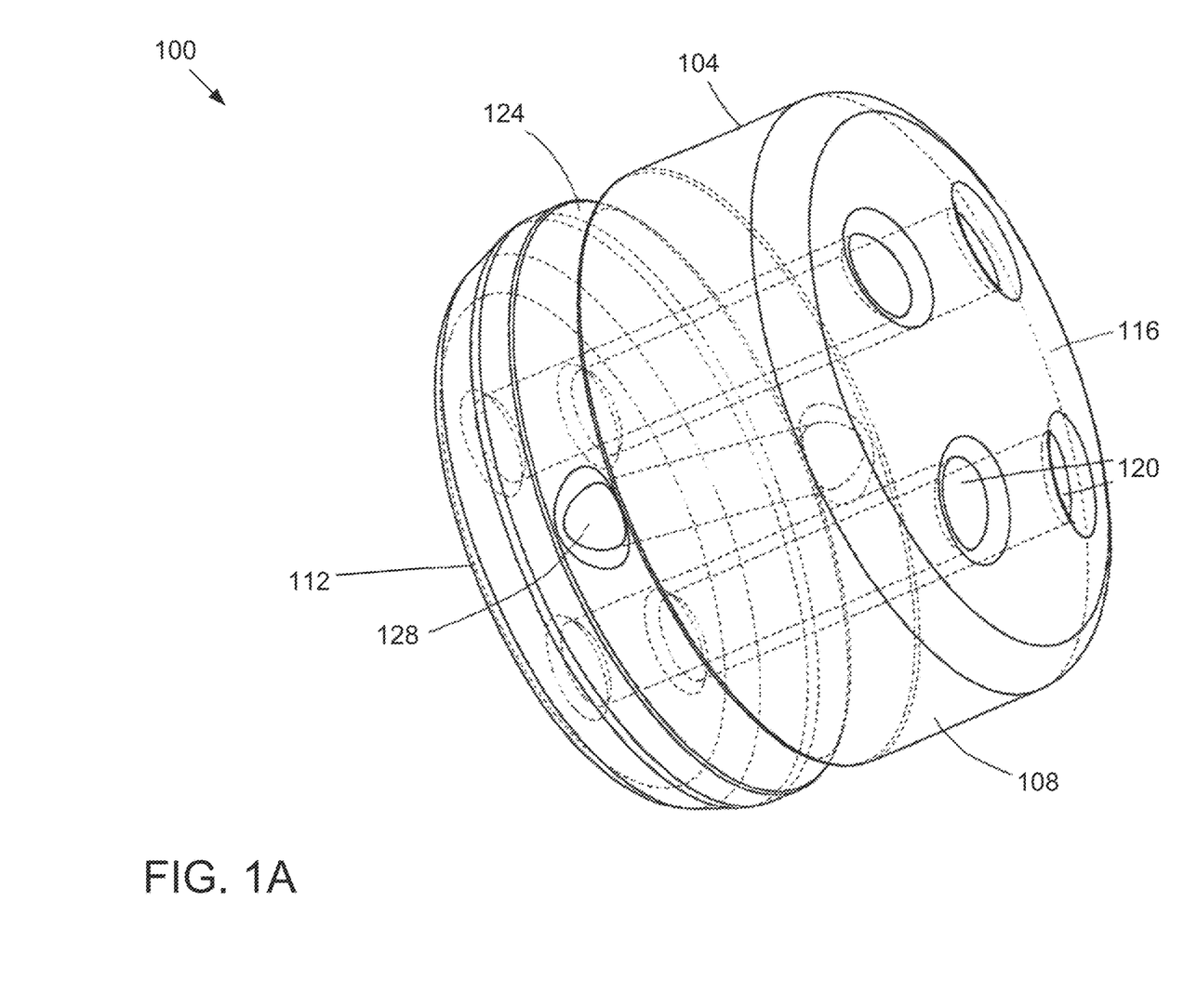
FIGS. 1A-1C depict various views of an embodiment of the present devices for anchoring a suture to a bone and/or repairing a joint by augmenting an articular surface of the bone.
Figure 1B:
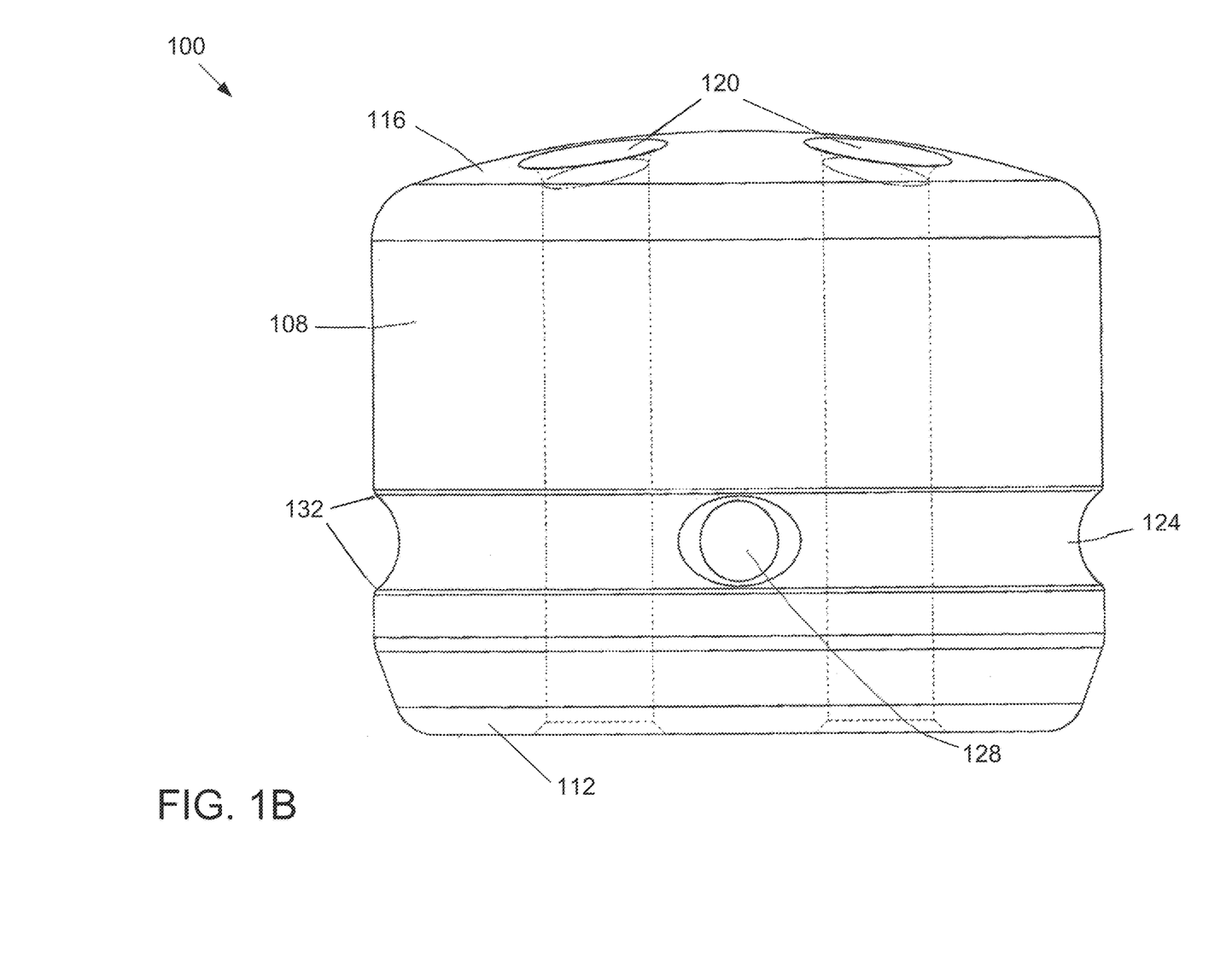
Figure 1C:
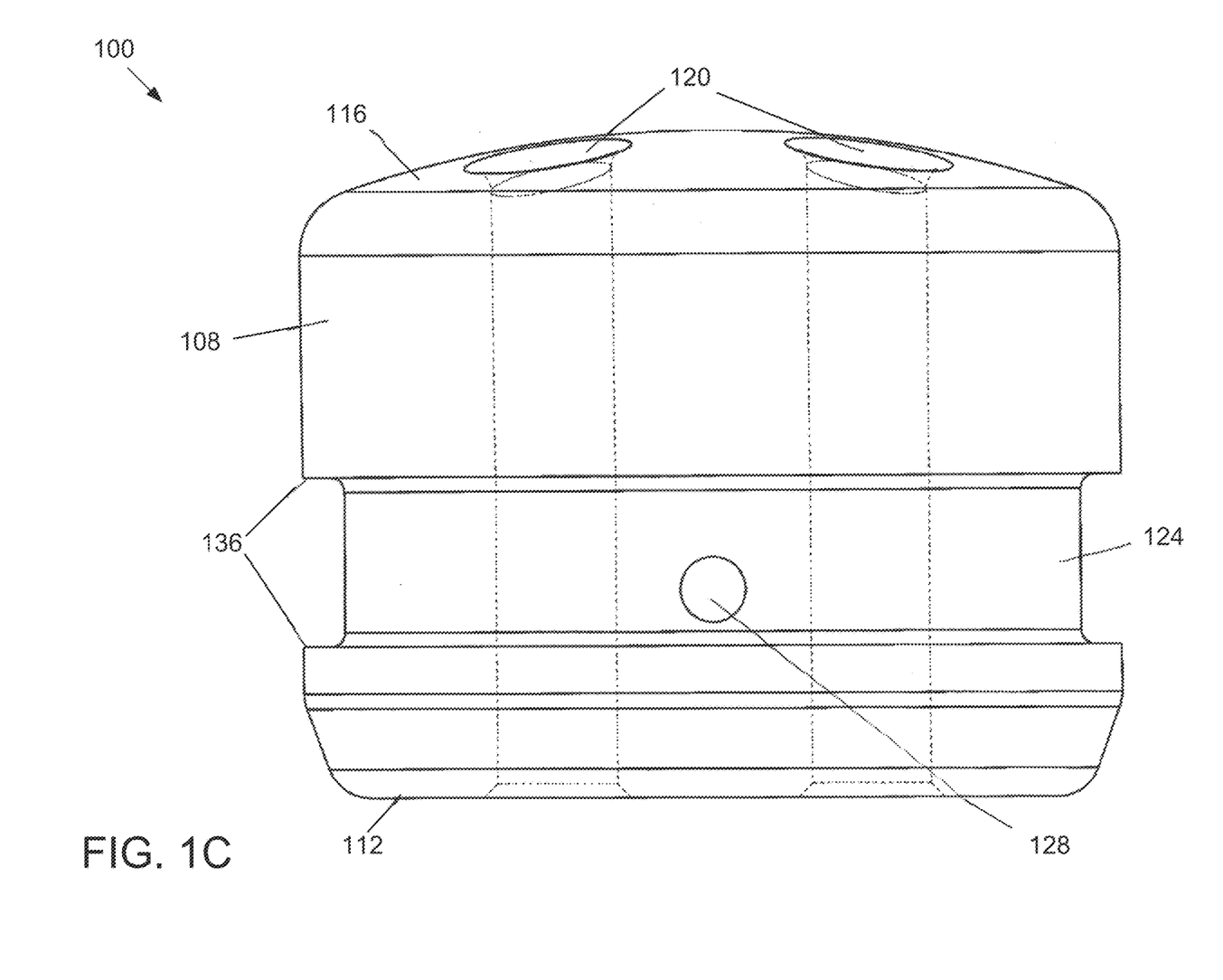

Referring now to the drawings, and more particularly to FIGS. 1A-1C, shown therein and designated by the reference numeral 100 is one embodiment of the present devices for repairing a joint by suturing biological matter to an articular surface of a bone (e.g., to repair a Hill-Sachs fracture). In the embodiment shown, device 100 comprises a pre-formed body 104 having a substantially cylindrical shape. More particularly, in this embodiment, body 104 comprises a peripheral surface 108 extending between a coupling end 112 of the body and a surface end 116 of the body. In this embodiment, peripheral surface 108 is substantially planar. In some embodiments, peripheral surface 108 is substantially cylindrical and coupling end 112 is substantially planar. A portion (e.g., a majority, as shown, and/or up to all) of peripheral surface is perpendicular to coupling end 112. In this embodiment, a portion of peripheral surface 108 adjacent coupling end 112 is angled to taper toward the coupling end (e.g., to facilitate insertion of body 104 into an opening in a bone. In other embodiments, peripheral surface 108 and/or coupling end 112 can have other shapes that permit body 104 to function as described in this disclosure. For example, peripheral surface 108 and/or coupling surface 112 can comprise dimples, ridges, threads, and/or the like.

In the embodiment shown, at least a portion (e.g., a majority, as shown, and/or up to all) of surface end 116 is convex such that, when body 104 is coupled into a mating cavity of a bone adjacent to a selected type of human joint socket, surface end 116 augments the articular surface of the bone. For example, for a body 104 configured to repair an articular defect in a humeral head, concave surface 116 can be shaped to replicate (or nearly replicate more nearly than the defect it replaces) the natural curvature or profile of the undamaged articular surface of the humeral head. Coupling surface 116 can be shaped or profiled to augment the articular surface of any suitable joint.

In the embodiment shown, body 104 has a maximum transverse dimension (across the body between diametrically opposed portions of the peripheral surface) that is greater than its maximum length (across the body between coupling end 112 and surface 116). For example, the maximum transverse dimension (e.g., diameter, in the depicted embodiment) can be greater than any one of, or between any two of: 100%, 110%, 120%, 130%, 140%, 150%, 160%, 170%, 180%, 190%, 200%, or more; of the maximum length. This ratio can improve stability of the body within a bone when the body is implanted to repair a defect in an articular surface (e.g., to augment an articular surface).

In some embodiments, body 104 comprises a biological material such as bone or soft tissue. In other embodiments, body 104 may comprise a metal or metallic material. In yet further embodiments, body 104 may comprise a polymer or plastic material. In some embodiments, body 104 may comprise multiple materials.

In the embodiment shown, body 104 defines a plurality of axial holes 120 to facilitate turning of the body once inserted into an opening or recess, as described in more detail below. In the embodiment shown, axial holes 120 extend entirely through body 104 between coupling end 112 and surface end 116. In other embodiments, axial holes 120 extend only partially through body 104 (i.e., not through coupling end 112). In the embodiment shown, a central longitudinal axis of each hole 120 is substantially parallel to a central, longitudinal axis of body 104, and perpendicular to a plane in which coupling end 112 lies. In other embodiments, axial holes 120 may be angled relative to the central, longitudinal axis.

In the embodiment shown, body 104 defines a groove 124 on peripheral surface 108. In this embodiment, groove 124 extends around the entire perimeter of peripheral surface 108. Groove 124 may be disposed at any location on peripheral surface 108 between coupling end 112 and surface end 116. As shown, groove 124 has a length, width, and depth large enough to receive or retain a portion of a suture within groove 124 when the suture is entirely wrapped around the body. In the embodiment shown, groove 124 is substantially perpendicular to the central, longitudinal axis of body 104.

In other embodiments, the body may define a plurality of grooves may be provided. For example, the body may define a first groove that wraps around a first portion of the perimeter of peripheral surface 108, and a second groove that wraps around a second portion of the perimeter of peripheral surface 108. In some embodiments, a plurality of grooves may be located in the same plane (e.g., perpendicular to the central, longitudinal axis of the body) or may be offset in different planes (e.g., that are spaced from one another along the longitudinal axis). In some embodiments, each groove may be substantially perpendicular to the central, longitudinal axis of body 104 or may be angled relative to the longitudinal axis of body 104. For example, the plurality of grooves may be disposed in an angled, helical configuration on peripheral surface 108. In embodiments having a plurality of grooves, each groove may be configured to receive or retain a separate suture.

In the embodiment shown, a suture hole 128 is formed through body 104 and configured to receive a suture with the suture passing all the way through the body and extending through both sides of the suture hole. In the embodiment shown, suture hole 128 extends entirely through body 104 between two opposite points on peripheral surface 108. In this embodiment, suture hole 128 can receive a suture that extends entirely through body 104 via suture hole 128. In the embodiment shown, a central longitudinal axis of suture hole 128 is perpendicular to the central, longitudinal axis of body 104 and/or axial holes 120. In the embodiment shown, suture hole 128 is substantially parallel to coupling end 112. However, in some embodiments, suture hole 128 may be angled relative to coupling end 112. The embodiment shown, suture hole 128 is aligned with groove 124 and extend through peripheral surface 108 on opposite sides of body 104 such that a suture passing through suture hole 128 will be aligned with groove 124 at the point at which the suture extends through the peripheral surface (e.g., to facilitate migration of the suture into the groove when the body is rotated as described below).

In other embodiments, suture hole 128 may be disposed at a point on peripheral surface 108 (e.g., aligned with a groove), and extend into and only partially through body 104 (without extending through a second point on peripheral surface 108). In these embodiments, a separate suture may extend into each suture hole (e.g., be coupled or attached to the body a point within the suture hole) and extend outwardly out of suture hole.

In some embodiments, the body defines multiple suture holes (e.g., in the same plane or in two or more planes offset from each other along the central, longitudinal axis of the body).

Groove 124 may be shaped in different ways to effectively retain the suture. In the embodiment shown in FIG. 1B, groove 124 is shaped such that groove 124 meets peripheral surface 108 at an angled junction 132. This configuration may reduce stress on the suture along the points of groove 124 but may provide a less-abrupt boundary for retaining the suture in the groove 124, which may be preferable for some applications. In the embodiment shown in FIG. 1C, groove 124 is shaped such that groove 124 meets peripheral surface 108 at a substantially perpendicular junction 136. This configuration provides a more abrupt boundary for the groove, which may be preferable for other applications. In the embodiment of FIG. 1C, groove 124 has a width that is at least (e.g., slightly larger than) twice the diameter of a suture with which the body is designed to be used, such that, for example, two portions of the suture may be disposed in a section of the groove without the two portions having to overlap each other in the radial direction (of the body). In this (FIG. 1C) embodiment, two portions of a suture can each wrap around more than 180 degrees of the perimeter of the body while maintaining only one thickness of suture between the body and a surface of bone defining a recess in which the body is disposed (as described in more detail below).

Figure 2:
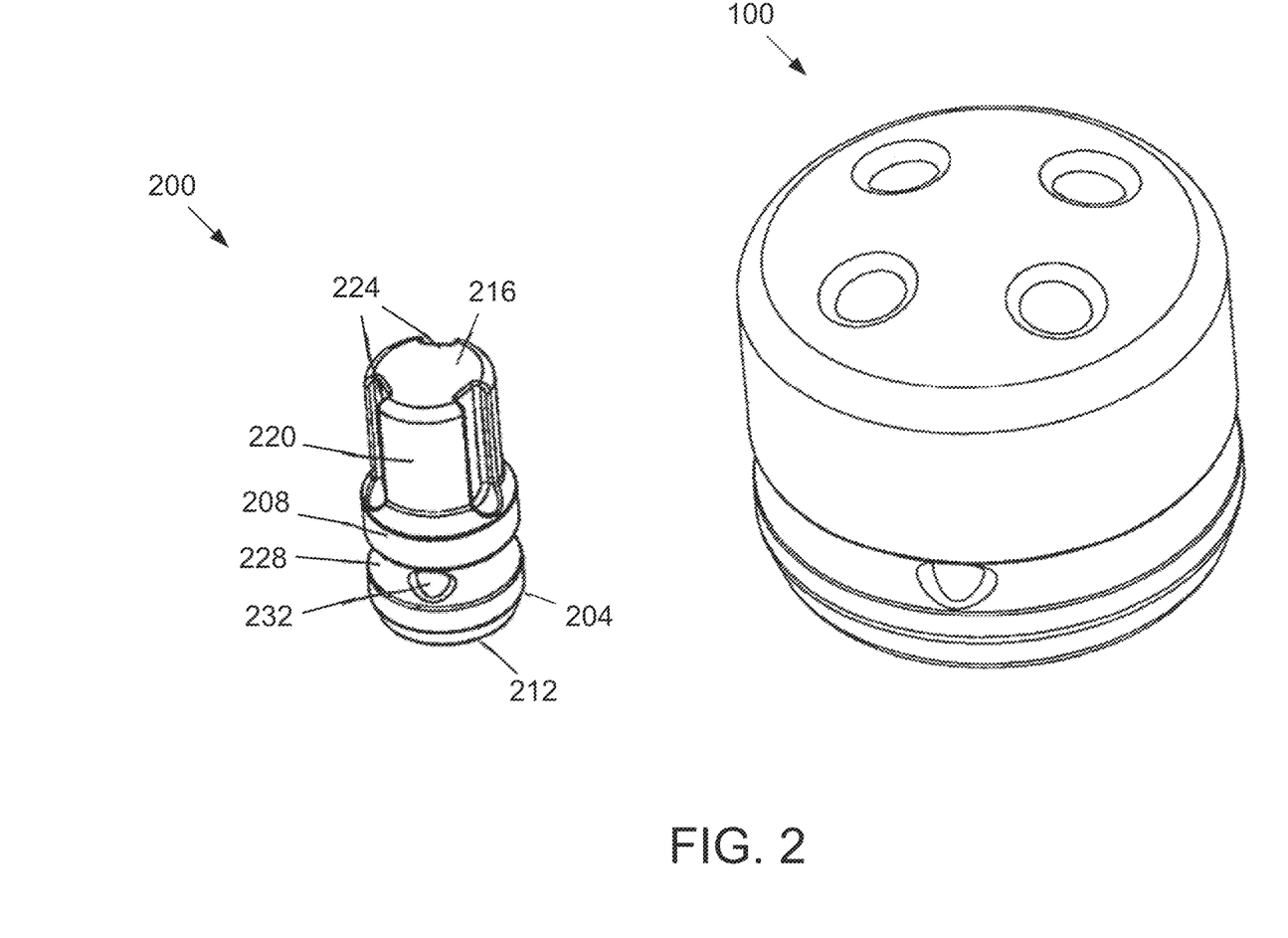
FIG. 2 depicts a perspective view of a second embodiment of the present devices for anchoring a suture to a bone.

Referring now to FIG. 2, a second embodiment 200 of the present devices is shown that is configured for anchoring tissue (e.g., soft tissue) to bone. For reference, device 200 is shown next to device 100 to illustrate certain differences between these depicted embodiments. Device 200 is substantially similar to device 100, and the following description of device 200 will therefore primarily focus on these differences. Device 200 comprises a pre-formed body 204 having a substantially cylindrical portion. More particularly, in this embodiment, body 204 comprises a peripheral surface 208 extending from a coupling end 212 of the body toward a distal end 216 of the body. In this embodiment, peripheral surface is substantially cylindrical and coupling end 208 is substantially planar. A portion (e.g., a majority, as shown, and/or up to all) of peripheral surface is perpendicular to coupling end 212. In this embodiment, a portion of peripheral surface 208 adjacent coupling end 212 is angled to taper toward the coupling end (e.g., to facilitate insertion of body 204 into an opening in a bone. In other embodiments, peripheral surface 208 and/or coupling end 212 can have other shapes that permit body 204 to function as described in this disclosure. For example, peripheral surface 208 and/or coupling surface 212 can comprise dimples, ridges, threads, and/or the like.

Rather than axial holes, in the embodiment shown, body 204 (at distal end 216) defines a male profile configured to be received in a recess of a driver with a corresponding female shape. More particularly, in this embodiment, body 204 defines a coupling surface 220 extending from distal end 216 toward coupling end 208, as shown, and further defines a plurality of axial grooves 224 configured to receive ridges of a driver such that rotation of the driver can rotate the body (204).

Body 208 also defines a groove 228 (similar to groove 124 of device 100) and one or more suture holes 232 (similar to suture holes 128 of device 100).

The primary difference between device 200 and device 100 is that device 200 is configured to anchor tissue to bone rather than to augment an articular surface. For example, in the embodiment shown, body 200 has a smaller transverse dimension (across the body between diametrically opposed portions of the peripheral surface) because it need no provide a surface against which a bone will slide. In some embodiments, the smaller diameter may help resist sliding of a suture relative to the body (204) and can thereby improves its function as an anchor. Due in part to this smaller transverse dimension and the use of a male coupling profile (rather than axial holes 120) for driving the device, body 204 has a maximum length (across the body between coupling end 112 and surface 116) that is greater than its maximum transverse dimension. For example, the maximum length (e.g., diameter, in the depicted embodiment) can be greater than any one of, or between any two of: 100%, 110%, 120%, 130%, 140%, 150%, 160%, 170%, 180%, 190%, 200%, or more; of the maximum transverse dimension.

Figure 3A:
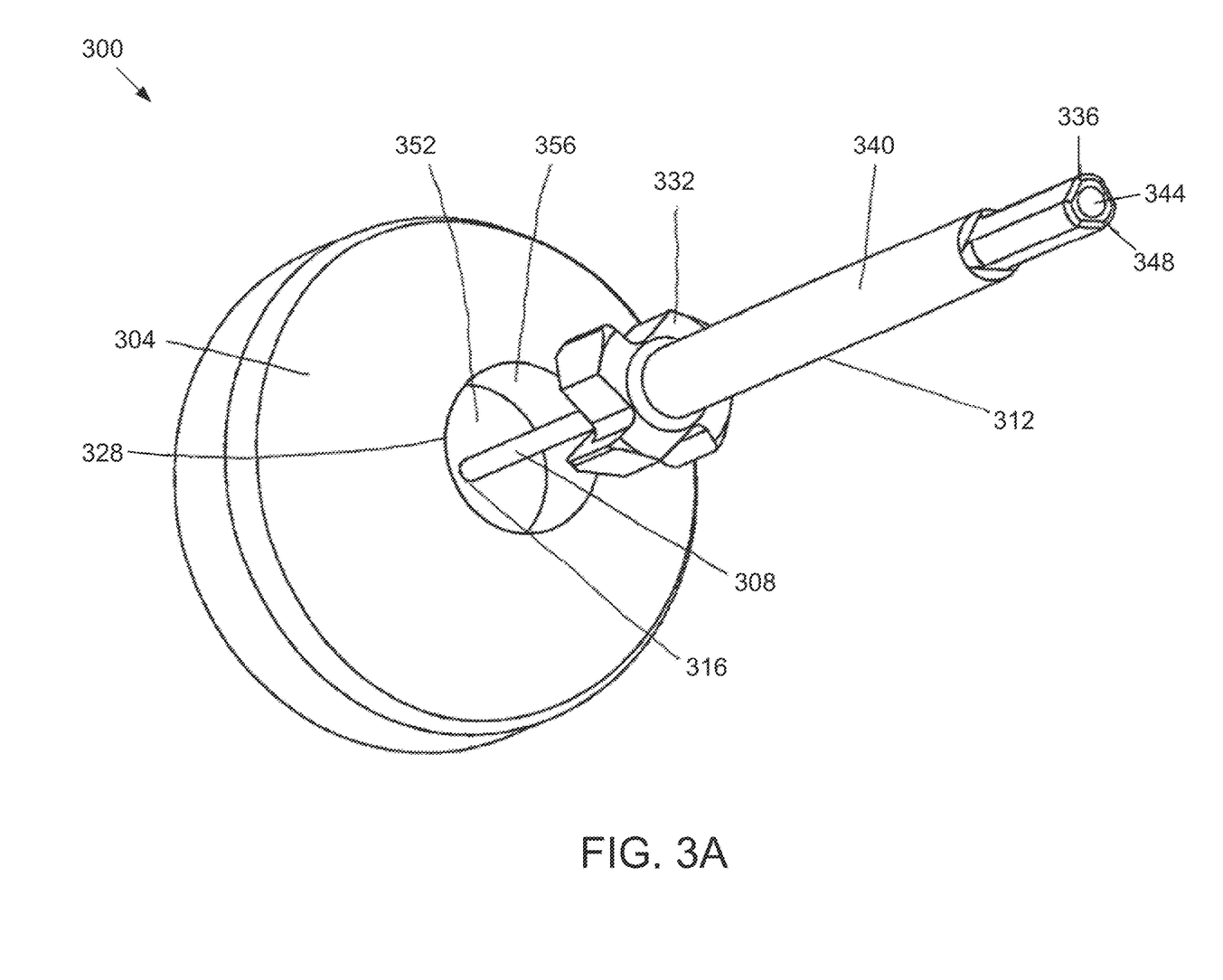
FIGS. 3A-3B depict perspective views of embodiments of apparatuses for preparing a bone to be coupled to the devices of FIGS. 1A-1C or FIG. 2.
Figure 3B:
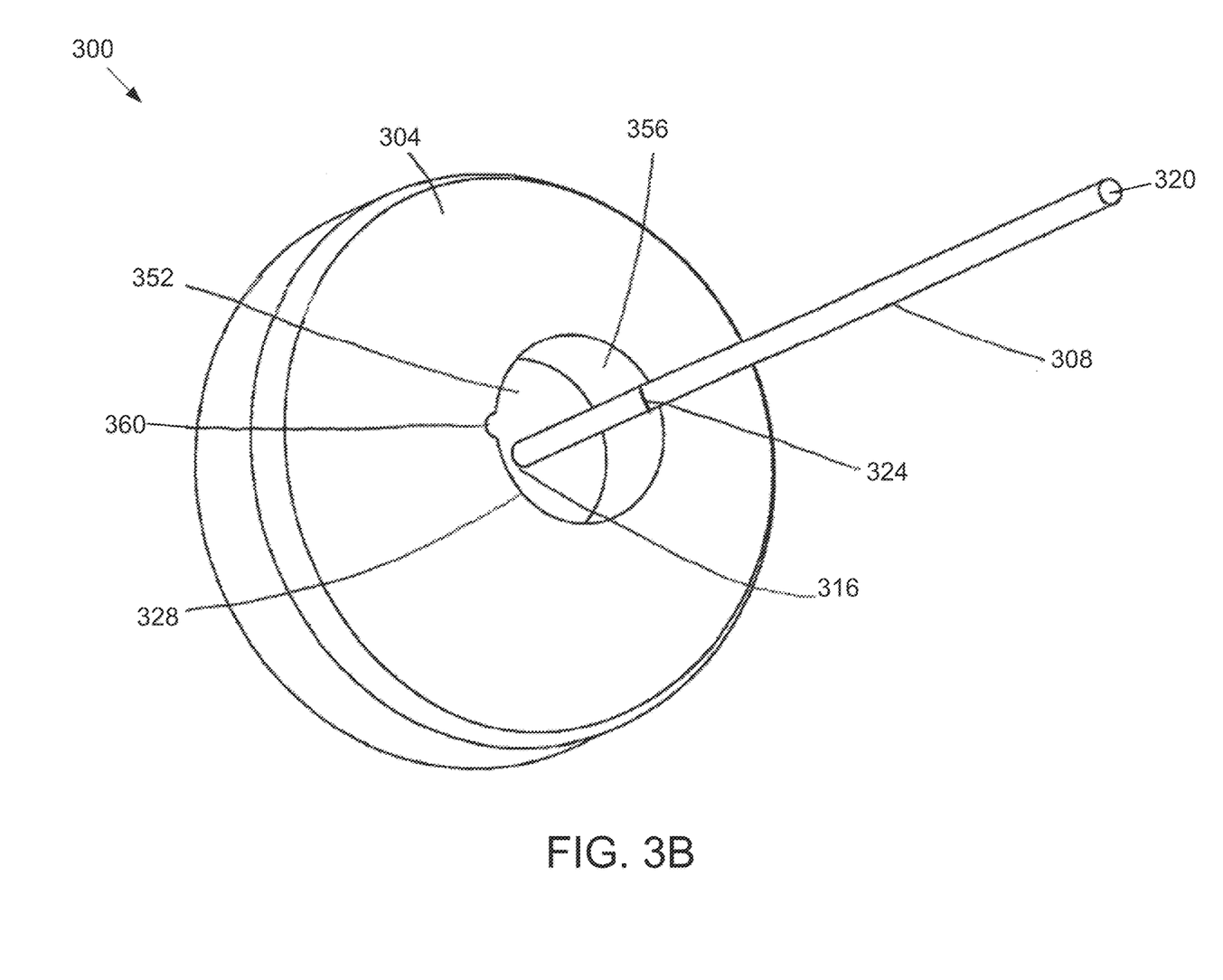

Referring now to FIGS. 3A-3B, 4A-4D, and 5, shown therein are various components of the present apparatuses for use with device 100 or 200, and various steps of exemplary embodiments of the present methods for such use. FIGS. 3A-3B depict perspective views of embodiments of an apparatus 300 for preparing a bone 304 to be coupled to device 100 or 200. In the embodiment shown, apparatus 300 includes pin 308 and reamer 312. In the embodiment shown, pin 308 has a proximal end 316, a distal end 320, and a depth indicator 324. In this embodiment, pin 308 is configured to be inserted into the articular surface of bone 304 such that distal end 320 extends a predetermined distance out of bone 304. In some embodiments, pin 308 comprises depth indicator 324. For example, depth indicator 308 can be aligned with the articular surface before mating cavity 328 is formed. For example, in the embodiment shown in FIG. 3B, depth indicator 324 comprises a line or other mark printed, engraved, etched, or otherwise visible at a selected point on pin 308. In some embodiments, proximal end 316 of pin 308 comprises a sharp tip to penetrate bone 304. The sharp tip may have smooth sides or may be threaded such that pin 308 can be inserted to a desired depth relative to bone 304 and substantially maintain the position of pin 308 relative to bone 304.

In the embodiments shown, reamer 312 is configured to be disposed over distal end 320 of pin 308 when proximal end 316 of pin 308 is disposed into bone 304. Reamer 312 may be rotated to remove a portion of bone 304 to form a mating cavity 328 in the articular surface of bone 304. For example, in the embodiment shown, reamer 312 comprises a proximal cutting end 332, a distal end 336, and a shaft 340 having an elongated passage 344 extending from cutting end 332 toward distal end 336 and configured to receive distal end 320 of pin 308. In this embodiment, cutting end 332 has a larger diameter relative to shaft 340 and is configured such that if the reamer is rotated around shaft 340, cutting end 332 will cut away a section of bone 304 to contour mating cavity 328 on bone 304. In the embodiment shown, shaft 340 comprises a shoulder 348 or other stop in passage 344 configured to contact distal end 336 of pin 308 to limit the depth to which cutting end 332 of reamer 312 can cut. For example, when pin 308 is inserted into bone 304 to a desired depth (e.g., indicated by depth indicator 324 of pin 308), shoulder 348 is configured to ensure that mating cavity 328 of bone 304 is formed at a desired depth or position. In the embodiment shown, cutting end 332 of reamer 312 is configured to shape mating cavity 328 to correspond to the shape of body 104 of device 100. For example, mating cavity 328 may be defined by a bottom surface 352 and a sidewall or side surface 356. Mating cavity 328 may be shaped by cutting end 332 of reamer 312 to enable coupling end 112 of body 104 to be disposed adjacent to bottom surface 352. Mating cavity 328 may also be shaped to enable peripheral surface 108 of body 104 to be disposed adjacent to side surface 356. In some embodiments, surface end 116 of body 104 may be disposed to match the plane of the articular surface of bone 304. In some embodiments, reamer 312 may also be configured to cut away a portion of bone 304 to form one or more notches 360 into side surface 356. After mating cavity 328 and any desired notches 360 are cut into bone 304, reamer 312 may be removed from pin 308 and pin 308 may be removed from bone 304.

In some embodiments, more than one mating cavity 328 may be created to enable more than one of devices 100 and/or 200 to be coupled to the same bone 304 or to different bones in a region. Pin 308 and reamer 312 can be sized to create a mating cavity 328 of appropriate dimensions to receive the corresponding device.

Figure 4A:
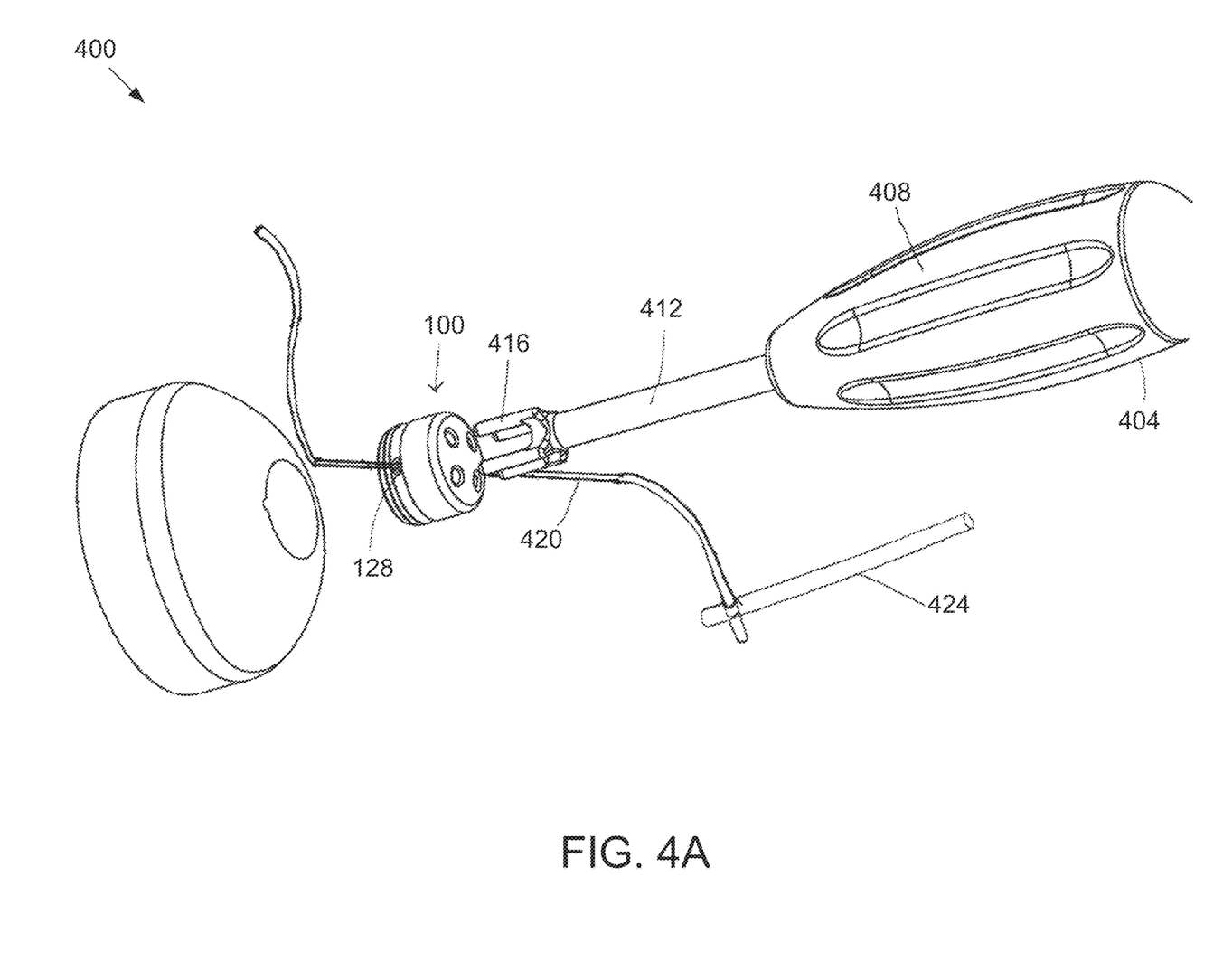
FIGS. 4A-4D depict perspective views of stages of the present methods of anchoring a suture to a bone and/or repairing a joint by affixing biological matter to augment an articular surface of the bone.

FIGS. 4A-4D and 5 depict an embodiment of the present methods. FIG. 4A depicts a perspective view of embodiments of an apparatus 300 for coupling device 100 or 200 to bone 304. In the embodiment shown, apparatus 400 includes removable driver 404 having handle 408, shaft 412, and a plurality of prongs 416. In this embodiment, handle 408 is coupled in fixed relation to shaft 412, and prongs 416 are disposed at a distal end of the shaft. In other embodiments, handle 408 may be configured to move relative to shaft 412 (e.g., via a ratchet mechanism). In other embodiments, the driver may include any structure (e.g., alternative to prongs). For example, while FIG. 4A shows an embodiment using device 100, device 200 is coupled to the bone in a similar manner, and the driver can readily be configured for use with device 200, such as, for example, with three prongs 316 corresponding to grooves 224 or with a female driver cavity having a profile corresponding to surface 220 and grooves 224.

As shown in FIG. 4A, suture 420 is inserted through suture hole 128 and is pulled through the suture hole until a substantially equal portion of suture 420 extends from suture hole 128 on either side of device 100. In some embodiments, suture 420 may extend in unequal lengths from each side of the suture hole. In other embodiments (not shown) having a plurality of suture holes, one or more sutures 320 may extend from each hole and may be configured to have substantially equal portions of suture 320 extending from each respective suture hole.

Figure 4B:
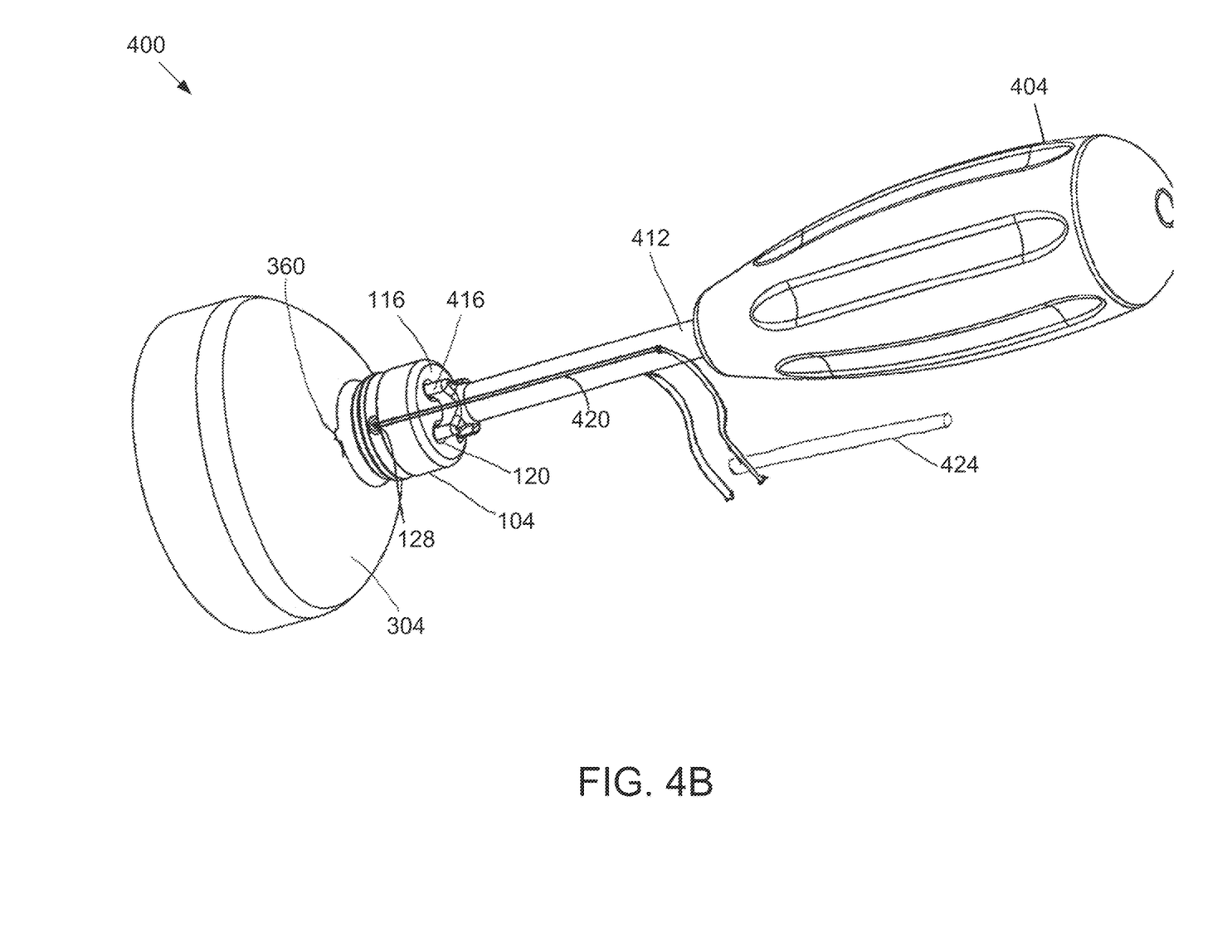
Figure 4C:
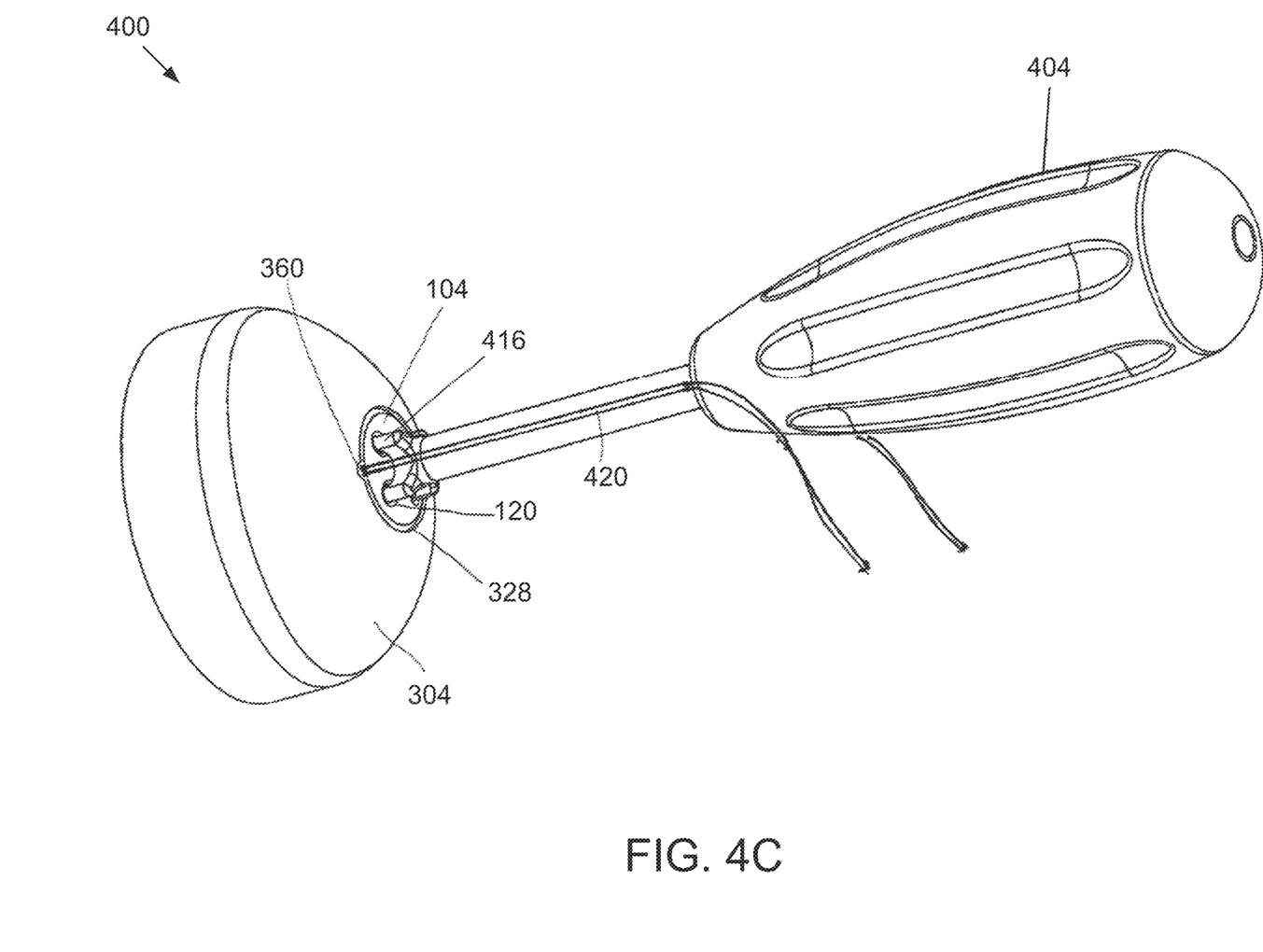
Figure 4D:
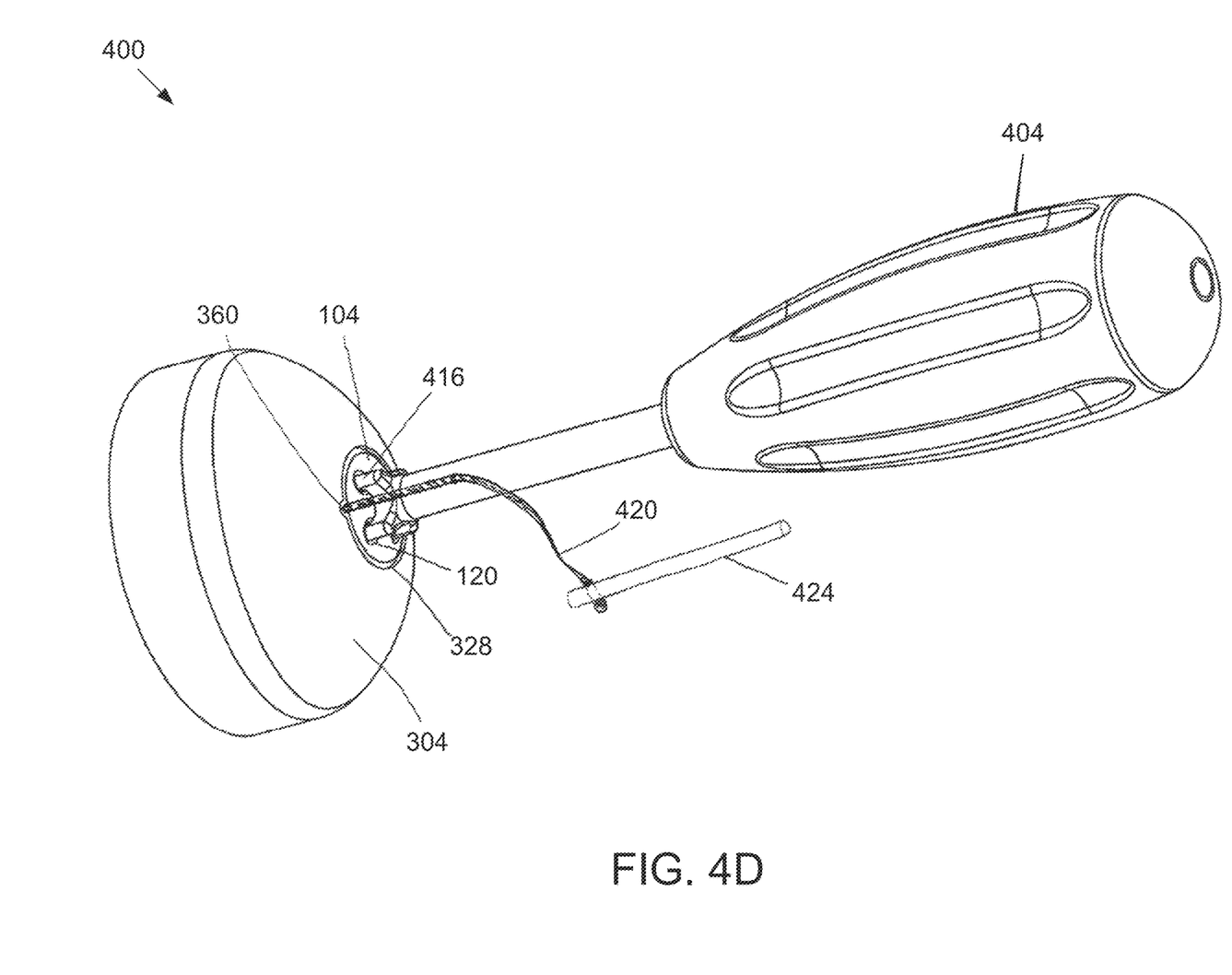

As shown in FIG. 4B, prongs 416 are inserted into the plurality of axial holes 120 in body 104. In some embodiments, prongs 416 may lock into axial holes 120. In the embodiment shown, suture 420 may be held taut by tensioning the ends of suture 420 along the longitudinal axis of body 104 and shaft 412, and suture 420 and suture hole 128 are aligned with corresponding notches 360 to position body 104 for insertion into mating cavity 328. Body 104 is then inserted into mating cavity 328 until coupling end 112 lies adjacent to bottom surface 352, peripheral surface 108 faces side surface 356, and surface end 116 augments the articular surface of bone 304. Once inserted, suture 420 may initially remain aligned with notch 360 and prongs 416 remain in holes 120. Driver 404 can then be rotated to rotate body 104 within mating cavity 328. As driver 404 is rotated, prongs 416 apply force to axial holes 120 to cause body 104 to rotate. In the embodiment shown, body 104 is rotated in a clockwise direction. In other embodiments, body 104 may be rotated in a counterclockwise direction. As shown in FIGS. 4C-4D, as body 104 rotates, suture 420 is drawn down into mating cavity 328 between the body and side surface 356 that defines the mating cavity (e.g., each portion of the suture may slide along a corresponding notch 360).

Figure 5:
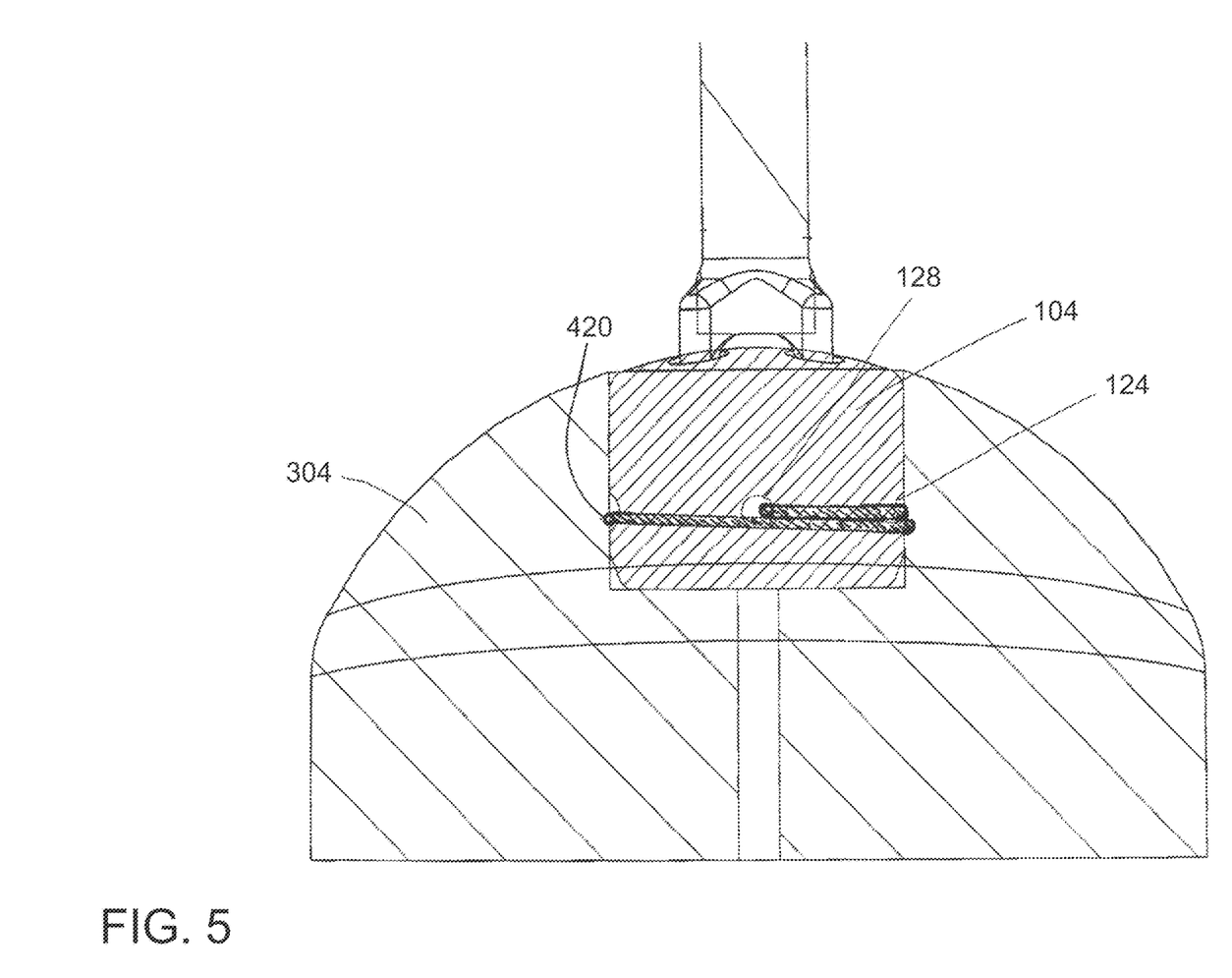
FIG. 5 depicts a partially cutaway side view of a bone with the device of FIGS. 1A-1C coupled to and/or augmenting the articular surface of the bone using the method of FIGS. 4A-4D.

In the embodiment shown in FIG. 5, as body 104 is rotated, suture 420 is collected into and retained by groove 124. In the embodiment shown, suture 420 wraps around body 104 inside groove 124 and draws the ends of suture 420 toward mating cavity 328. As the suture 420 is drawn into mating cavity 328, body 104 may become secured into mating cavity 328 by friction or pressure created by compression of the suture between body 104 and surface 356. For example, a friction locking effect may be created by suture 420 as body 104 is rotated to secure body 104 into mating cavity 328. More particularly, as the suture drawn into the space between body 104 and surface 356, the friction between the suture and body 104, and between the suture and surface 356 resists axial movement of the body out of the cavity, and also resists rotation of body 104 relative to surface 356. As bone 204 heals, bone material may grow around body 104 to permanently secure body 104 to bone 304.

The manner in which the depicted structure draws the suture into the space between body 104 and surface 256 can be advantageously used to anchor tissue 424 (e.g., soft tissue) to bone. For example, as shown FIGS. 4A-4B, each loose end of a suture 420 can be coupled to tissue 424 and the body (104 or 204) inserted into the mating cavity such that, as the body is rotated, the tissue to which the suture is anchored (e.g., a tendon) is drawn toward the mating cavity at the same time the suture is being drawn into the mating cavity to secure the body. Some embodiments of the present kits comprise one or more items selected from the list consisting of: an embodiment of the present devices (e.g., 100), one or more pins 308 (e.g., of different lengths), an embodiment of the present reamers (e.g., 312), an embodiment of the present drivers (e.g., 404), and one or more sutures 420. In some embodiments, the components of the kit are sterile and/or disposed in a sealed package (e.g., a polymer tray with a sealing file).

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices, apparatuses, kits, and methods are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A device comprising:
   a cylindrical body comprising a coupling end that is substantially planar, a surface end having a convex shape, and a peripheral surface extending at least partially between the coupling end and the surface end, the body defining a plurality of axial holes that extend through an entirety of the body from the surface end toward the coupling end, the body having a dimension in a transverse direction that is 100% to 200% of a length of the body, the body defining one or more suture holes extending inward from the peripheral surface, the body defining one or more grooves disposed on the peripheral surface, the one or more grooves configured to receive one or more sutures from the one or more suture holes such that the one or more sutures wrap around at least a portion of the one or more grooves to resist axial movement out of a mating cavity of a bone, the body configured to be coupled into the mating cavity of the bone adjacent to a selected type of human joint socket such that:
   the coupling end faces a bottom surface defining the mating cavity, the surface end augments an articular surface of the bone, and the peripheral surface faces a sidewall defining the mating cavity.

2. The device of claim 1, further comprising a coupling surface extending between the peripheral surface and the surface end.

3. The device of claim 1, further comprising the one or more sutures configured to attach to the body via the one or more suture holes.

4. The device of claim 1, where the one or more suture holes comprise a first suture hole having a first opening disposed on a first side of the peripheral surface and a second opening disposed on a second side of the peripheral surface, the second side opposite to the first side, the first suture hole extending through an entirety of the cylindrical body.

5. The device of claim 1, where the one or more grooves comprise a plurality of grooves each disposed in an angled helical configuration on the peripheral surface.

6. The device of claim 1, where the body defines the one or more suture holes extending inward from the peripheral surface, each of the one or more suture holes configured to receive a suture.

7. The device of claim 6, where the one or more suture holes are aligned with the one or more grooves.

8. The device of claim 1, where the body is configured to be removably coupled to a driver such that the body can be rotated via rotation of the driver.

9. The device of claim 8, where the plurality of axial holes are configured to receive a plurality of prongs of the driver such that the body can be rotated via rotation of the driver.

10. The device of claim 1, where the body comprises a biological material.

11. The device of claim 10, where the biological material comprises bone.

12. The device of claim 1, where the one or more grooves comprise a single groove configured to receive a single suture from a single suture hole such that the single suture wraps around at least a portion of the single groove to resist axial movement out of the mating cavity of the bone.

13. The device of claim 1, where each of the one or more grooves has a width that is substantially twice the width of a suture.

14. The device of claim 1, where each of the one or more grooves meets the peripheral surface at a substantially perpendicular junction.

15. A kit comprising:
   the device of claim 1; and
   an apparatus comprising:
      a driver having a shaft, a handle attached to the distal end of the shaft, and a plurality of prongs attached to the proximal end of the shaft, the plurality of prongs configured to be inserted at a surface side of a body, the plurality of prongs further configured to lock into axial holes in the surface side of the body,
   where the device and apparatus are disposed in one or more sealed packages.

16. A method of one or more of anchoring a suture to a bone and repairing a human joint, the method comprising:
   inserting a cylindrical body of a device into a mating cavity formed in a bone, where the body comprises a coupling end that is substantially planar, a surface end having a convex shape, and a peripheral surface extending between the coupling end and the surface end, the body defining a plurality of axial holes that extend through an entirety of the body from the surface end toward the coupling end, the body having a dimension in a transverse direction that is 100% to 200% of a length of the body, the body defining one or more suture holes extending inward from the peripheral surface, the device having one or more sutures extending out of the one or more suture holes, the body defining one or more grooves disposed on the peripheral surface, the one or more grooves configured to receive the one or more sutures;
   where the body is inserted into the mating cavity such that:
      the coupling end faces a bottom surface defining the mating cavity,
      the surface end augments an articular surface of the bone, and
      the peripheral surface faces a sidewall defining the mating cavity; and the one or more sutures are at least partially disposed between the body and the sidewall to wrap around at least a portion of the one or more grooves to resist removal by axial movement of the body from the mating cavity.

17. The method of claim 16, where the mating cavity formed in the bone is disposed adjacent to a human joint socket.

18. The method of claim 16, where the one or more sutures are coupled to soft tissue.

19. The method of claim 16, further comprising:
tensioning the one or more sutures along a longitudinal axis of the body.

* * * * *